United States Patent [19]

Murray et al.

[11] 3,993,074

[45] Nov. 23, 1976

[54] MONOLITHIC SANITARY DEVICE

[76] Inventors: Jerome L. Murray, 652 First Ave., New York, N.Y. 10016; Frances R. Gardiner, 43 Park Road, Sparta, N.J. 07871

[22] Filed: May 7, 1975

[21] Appl. No.: 575,203

[52] U.S. Cl. .................................. 128/286; 128/287; 128/290 R; 264/45.1

[51] Int. Cl.$^2$ .......................................... A61F 5/44

[58] Field of Search ................ 128/290 R, 286, 284, 128/290 P, 290 W, 287, 296; 264/45.9

[56] References Cited

UNITED STATES PATENTS 2,698,016 12/1954 Andrade et al. .................... 128/286
3,563,243 2/1971 Lindquist ........................... 128/287
3,901,240 8/1975 Hoey .................................. 128/296

*Primary Examiner*—Lawrence W. Trapp
*Attorney, Agent, or Firm*—Silverman and Jackson

[57] ABSTRACT

A monolithic sanitary device comprising a generally arcuate, boat-shaped structure prepared from a hydrophilic, highly absorbent, polymeric foam material which has been rendered fluid-impervious on one side thereof by a coating of an organic polymeric latex material. The device dispenses with the need of elaborate barrier layers, the various facing and backing sheets, as the foam material possess a texture which is acceptable to living tissue and the fluid-impervious latex coating prevents undesirable strike-through and assists in maintaining the structural integrity of the device.

17 Claims, 4 Drawing Figures

20
22
24
21
17
23
11
15
19
10

MONOLITHIC SANITARY DEVICE

BACKGROUND OF THE INVENTION

The present invention relates to the area of absorptive sanitary devices, and more particularly to sanitary devices comprising fluid-pervious and fluid-impervious components.

The preparation of sanitary devices has conventionally entailed the provision of an absorbent material in loose or fiberous form which is, in some manner, held together either by a fluid-impervious adhesive or by containment within a shroud comprising a fluid-pervious facing and a fluid impervious backing. Common absorbents comprised short-length cellulosic fibers in the form of bulky masses or compacted thin paper sheets. These materials tended to bunch up or shred upon wetting and caused the wearer great discomfort as well as allowing undesirable leakage or "strike-through" to occur.

In addition to the above varieties of devices, extensive numbers of sanitary products employ what is called a baffle or barrier layer comprising a fluid-impervious sheet or the like which is placed centrally within the product and surrounded with absorbent material on both sides, for the purpose of diverting and equally distributing the flow of fluid throughout the absorbent material. The production of products of this type is expensive, and the results obtained by pads employing baffles are not so improved.

Recently, the use of hydrophilic foam material has been proposed in an effort to obviate some of the prior art difficulties. Specifically, U.S. Pat. No. 3,563,243 by Lindquist, proposes to employ a hydrophilic polyurethane material as the absorbent in a sanitary sheet product. Patentee, however, found that the foams employed therein tend undesirably to change size and shape upon absorption of substantial liquid, and, accordingly, preferred to enclose the foams within backing and facing members, alone or in combination with other foams or cellulose crepe tissue layers.

The use of backing and facing members results in higher product cost resulting from the additional time and effort required to manufacture the devices, and the cost of the starting materials.

SUMMARY OF THE INVENTION

In accordance with the present invention, a monolithic sanitary device is disclosed which comprises a generally arcuate boat-shaped structure prepared from a hydrophilic, highly absorbent polymeric foam material which has been rendered fluid-impervious on one side thereof by a coating of an organic polymeric latex material.

The device further includes means for support on a body in the instance where it is employed as a sanitary napkin comprising a first length of elastic string defining a first loop attached to a longitudinal end of said device, and a second length of elastic string free at both ends and associated at its center with the opposite longitudinal end of said device. One of the free ends of said second length of string defines a second loop, and the other of said free ends is provided with a U-shaped hook. In operation, both ends of said second length are extended around the mid-section of the body, and meet, whereupon the free end bearing said hook is passed through said second loop and engages said first loop, to secure the device in position.

The sanitary device of this invention is easily fabricated and maintains its structural integrity in contact with moisture without the assistance of external constraints such as backing and facing members.

Accordingly, it is a principal object of the present invention to provide a sanitary device which is comfortable, highly absorptive and inexpensive to manufacture.

It is a further object of the present invention to provide a device as aforesaid which comprises a monolithic structure prepared from a hydrophilic foam coated on one surface thereof with liquid impervious latex material.

It is yet a further object of the present invention to provide a sanitary device as aforesaid which is structurally stable in use and effectively eliminates fluid leakage.

Other objects and advantages will become apparent from a consideration of the following description and accompanying drawings.

DETAILED DESCRIPTION

Figure 1:
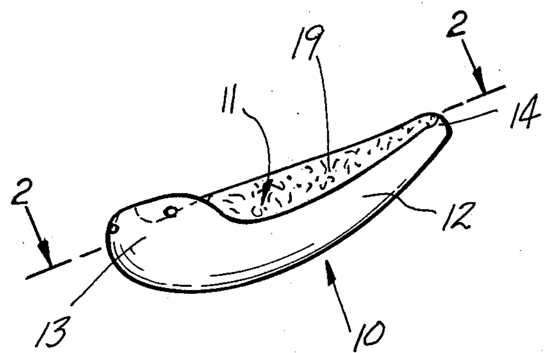
FIG. 1 is a perspective view of the sanitary device of the invention.

Referring to the drawings, FIG. 1 represents a perspective view of a sanitary device 10 comprising a generally arcuate, boat-shaped structure 11 prepared from a hydrophilic absorbent polymeric foam segment, which is absorbent on its upper surface 19 but has been rendered fluid-impervious on underside or lower surface 12 by the application thereto of a polymeric latex coating.

The polymeric foams of the present invention may be hydrophilic polyurethane foams or hydrophilic formaldehyde polyvinylalcohol foams. It is preferred, however, that the foam be a hydrophilic polyurethane foam. A commercially available hydrophilic polyurethane foam is marketed under the tradename Acquell and is available from the Scott Paper Company. This is a polyurethane foam produced by the reaction of a polyesterdiol and tolylene diisocyanate. The polyesterdiol also contains adipic acid and block copolymers of polyoxyethylene and polyoxypropylene.

Another foam which may be used in accordance with this invention, is prepared by, in a first step, forming a prepolymer by the reaction of polyethylene glycol and trimethylol propane in a mole ratio of about 2:0.125 to 2:2 respectively, followed by capping the reaction product at all hydroxy locations using tolylene diisocyanate consisting of about an 80/20 mixture of the 2,4 isomer to 2,6 isomer; and in a second step reacting 100 parts by weight of prepolymer with 30 parts by weight of water containing 5 parts by weight of polyoxyalkylene non-ionic surfactant. A particular non-ionic surfactant which has been found useful is one commercially available under the tradename Pluronic L-64 from the Wyandotte Chemicals Corporation. Although the above comprise the preferred hydrophilic urethane foam materials, other useful hydrophilic urethane foams are produced by varying the above prepolymer to water ratio, as well as varying the water surfactant ratio.

The polymeric foams of the invention may be formed into the shape depicted in the figures, by any of the several molding methods that are conventionally practiced with foam materials, such as injection molding or casting into an appropriately shaped cavity, and the invention should not be construed as limited thereby.

After the foam material is prepared to shape, it is given a coating of a non-toxic latex composition, over underside or lower surface 12 to render surface 12 fluid-impervious. Suitable latex coating materials may include, for example, polyolefins, such as synthetic rubber, polyethylene, polystyrene, ABS resins, ethylene-vinyl acetate, acrylic and vinyl ester latexes, silicone resins comprising the polysiloxanes, and the like. The coatings may be applied by conventional techniques including, without limitation, spraying, dipping and brushing to a thickness sufficient to enter and block all of the pores on underside surface 12.

Figure 2:
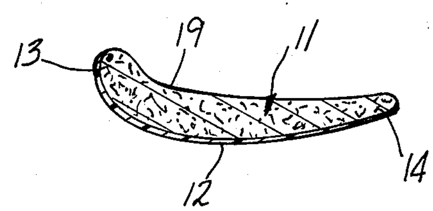
FIG. 2 is a sectional view taken through line 2—2 of FIG. 1.

Referring now to FIG. 2, coated surface 12 is clearly depicted, and can be seen to have been uniformly covered by latex material. Due to the open-celled structure of the foam, a small amount of latex may infiltrate surface 12, however, the amount is negligible and would have no effect on the absorptive capacity of the device.

In FIG. 2, device 10 comprises a sanitary napkin and can be seen to possess a thickened front end portion 13, which is designed to accommodate the preponderance of the menstrual flow. Device 10 is gradually reduced in thickness and width as it extends back to rear end portion 14 (see also FIG. 1), to assure comfortable fit and as there is obviously little absorbency required in that area. As noted before, the foam of the present invention is capable of maintaining its structural stability during menstrual flow which assures the user that device 10 will retain its dry shape as depicted in the figures.

Figure 3:
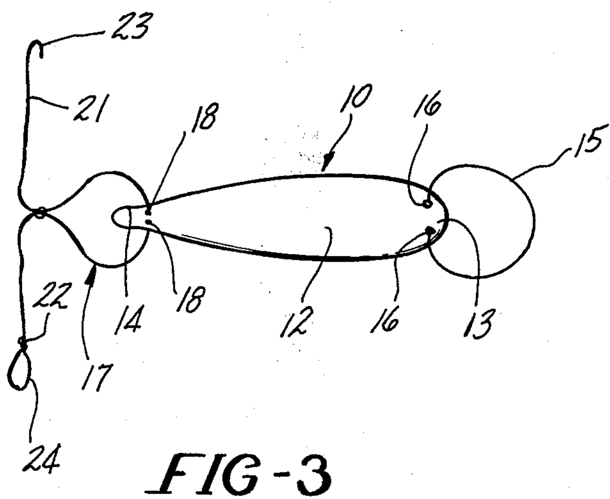
FIG. 3 is a bottom view of the device of the invention including a body support means.

Turning to FIG. 3, the sanitary device of the invention is shown provided with a special body support means comprising, generally, a pair of cooperating elastic strings. Particularly, first elastic string 15 defines a closed loop which is formed by passage of an elastic strand through openings 16 provided in front end portion 13 of device 10, followed by knotting or otherwise fastening together the ends of the strand. Second elastic string 17 is first threaded through openings 18 provided in rear end portion 14, then knotted at 20 so as to maintain free ends 21 and 22. Free end 21 is provided with U-shaped hook 23 for grasping loop 15, and free end 22 defines second loop 24 through which hook 23 passes on its way to loop 15.

Figure 4:
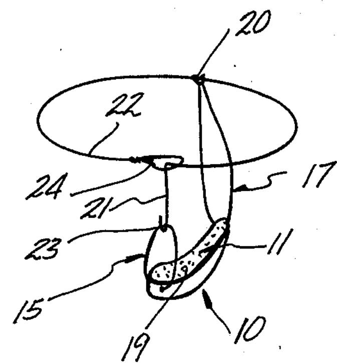
FIG. 4 is a perspective view showing the device of FIG. 3 with the body support means in operable association.

The above description is better understood with reference to FIG. 4, wherein the respective elements of the body support means are shown in place. Thus, device 10 is shown cradled and suspended by loop 15 and strand 17. Strand 17 travels up to the rear of the waist where it divides at knot 20, and proceeds in opposing circumferential directions until meeting at the front thereof, where hook 23 passes through loop 24 and travels downward to grasp loop 15. This simple mechanism is inexpensive to manufacture and provides a secure, comfortable fit for the user.

The sanitary devices of the present invention may be employed as described above, or may also contain, as desired, various suitable additives such as deodorants, disinfectants, perfumes, medicaments, emollients, pigments and/or dyes. Though the size and shape of the devices have been shown suited for use as sanitary napkins, it is contemplated that the devices could be used in the treatment of hemorrhoids and the like. Thus, the size and shape of the sanitary devices of this invention may vary widely to account for variations in locus of use and function.

Throughout the specification, all percentages of ingredients are expressed as percent by weight.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A monolithic sanitary device comprising an arcuate, boat-shaped structure prepared from a hydrophilic, absorbent polymeric foam material coated on one side thereof with a fluid-impervious organic polymeric latex.

2. The device of claim 1 wherein said hydrophilic foam comprises a polyurethane.

3. The device of claim 1 wherein said latex is prepared from a material selected from the group consisting of polyolefins, polyacrylates, ethylene-vinyl acetate copolymers, ABS resins, and silicone resins.

4. The device of claim 3 wherein said latex comprises a silicone resin.

5. The device of claim 1 further including means attached thereto for supporting said device on a body.

6. The device of claim 5 wherein said body support means comprises a pair of elastic strings, each attached to said device at opposite longitudinal ends thereof.

7. The device of claim 6 wherein one of said strings defines a first loop, and the other of said strings is joined at one point a short distance beyond said respective longitudinal end with two strands emerging from said juncture, wherein one of said strands terminates in a second loop, and the other of said strands terminates in a hook, whereby said strand bearing said hook is adapted to pass through said second loop, and engage said first loop.

8. The device of claim 7 which comprises a sanitary napkin.

9. The device of claim 1 further containing an additive selected from the group consisting of deodorants, disinfectants, perfumes, emollients, medicaments, pigments, dyes and mixtures thereof.

10. The device of claim 1 wherein said boat-shaped structure comprises an upper surface possessing a lesser curvature and a lower surface possessing a greater curvature, and said latex is coated upon said lower surface.

11. A method for the preparation of a monolithic sanitary device which comprises:

A. providing an absorbent, hydrophilic organic polymeric foam material;

B. forming said foam material into an arcuate, boat-shaped structure; and

C. coating said structure on one side thereof with a fluid-impervious organic polymeric latex.

12. The method of claim 11 wherein said polymeric foam comprises a polyurethane.

13. The method of claim 11 wherein said foam is formed into said structure by injection molding.

14. The method of claim 13 wherein said latex comprises a silicone resin.

15. The method of claim 11 wherein said latex is prepared from a material selected from the group consisting of polyolefins, polyacrylates, ethylene-vinyl acetate copolymers, ABS resins, and silicone resins.

16. The method of claim 11 wherein said structure is coated by spraying with said resin.

17. The method of claim 11 wherein said structure is coated by dipping in a bath of said resin.

* * * * *